United States Patent
Weir et al.

(10) Patent No.: US 10,794,453 B2
(45) Date of Patent: Oct. 6, 2020

(54) HIGH TORQUE DENSITY MINIATURE LAMINAR GEAR TRANSMISSION

(71) Applicant: The Regents of the University of Colorado, Denver, CO (US)

(72) Inventors: Richard Weir, Longmont, CO (US); Stephen Huddle, Northglenn, CO (US); Barathwaj Murali, Highlands Ranch, CO (US); Ozkan Celik, Cedar Park, TX (US)

(73) Assignees: THE REGENTS OF THE UNIVERSITY OF COLORADO, A BODY CORPORATE, Denver, CO (US); COLORADO SCHOOL OF MINES, Golden, CO (US)

( * ) Notice: Subject to any disclaimer, the term of this patent is extended or adjusted under 35 U.S.C. 154(b) by 6 days.

(21) Appl. No.: 16/366,733

(22) Filed: Mar. 27, 2019

(65) Prior Publication Data

US 2019/0301570 A1    Oct. 3, 2019

Related U.S. Application Data

(60) Provisional application No. 62/648,707, filed on Mar. 27, 2018.

(51) Int. Cl.
| | | |
|---|---|---|
| *F16H 1/46* | (2006.01) | |
| *F16H 3/64* | (2006.01) | |
| *F16H 57/02* | (2012.01) | |
| *F16H 3/52* | (2006.01) | |
| *F16H 57/023* | (2012.01) | |

(52) U.S. Cl.
CPC ............. *F16H 3/52* (2013.01); *F16H 57/023* (2013.01); *F16H 2057/02086* (2013.01)

(58) Field of Classification Search
CPC .... F16H 1/46; F16H 3/64; F16H 2057/02086; F16H 2057/033
See application file for complete search history.

(56) References Cited

U.S. PATENT DOCUMENTS

| | | | | |
|---|---|---|---|---|
| 3,334,811 A | * | 8/1967 | Sigl | G06M 3/022 235/103 |
| 6,402,653 B1 | * | 6/2002 | Jensen | B65G 23/08 475/149 |
| 7,296,495 B2 | * | 11/2007 | Quinn | F16H 1/46 475/330 |
| 7,404,782 B2 | * | 7/2008 | Kudoh | A61H 1/0237 475/337 |
| 2011/0241369 A1 | * | 10/2011 | Kamon | B25J 15/026 294/213 |
| 2015/0072828 A1 | | 3/2015 | Reuter | |
| 2019/0262989 A1 | * | 8/2019 | Cui | H02K 11/33 |

FOREIGN PATENT DOCUMENTS

JP          11037226 A  *  2/1999  ............... F16H 1/46

* cited by examiner

*Primary Examiner* — Tisha D Lewis
(74) *Attorney, Agent, or Firm* — Optima Law Group, APC; Thomas E. Jurgensen

(57) ABSTRACT

A miniturized laminar gear box possessing high torque densities and methods of manufacturing the same. The high torque density is possible by directing the output shaft of the planetary stages through the sun gear and behind the input shaft. This allows the input shafts of the planetary stages to face towards the interior of the gearbox and provides a rotary shaft for the spur stages housed in between the planetary stages.

4 Claims, 9 Drawing Sheets

HIGH TORQUE DENSITY MINIATURE LAMINAR GEAR TRANSMISSION

CROSS-REFERENCE TO RELATED APPLICATIONS

This application claims priority to U.S. Provisional Patent Application No. 62/648,707, filed Mar. 27, 2018.

FIELD OF THE INVENTION

The present invention relates to compact gear transmissions.

BACKGROUND

Commercially available miniature gearboxes supplied by companies such as Maxon Motors and Faulhaber Group generally have intermittent torque ratings that may require further reduction in order to reach the desired torques set by the designer. Thus, the currently available gearboxes lack sufficiently high torque densities for many applications that require the gearbox to fit into a small space.

Commercially available gears, such as those available from BostonGear or SDP-SI place further design limitations due to material strengths and additional design features such as hub dimensions and shaft sizes. Furthermore, the additional space/manufacturing requirements for the housing of commercial gear/gearbox components can add an extra degree of complexity to the overall design. This complexity often results in final gearboxes that are larger than necessary.

Thus, there is a need for a compact gearbox with high torque density. It will be apparent to those having skill in the art that such a gearbox would be difficult, if not impossible, to produce using standard manufacturing techniques. However, the compact, high torque density gearbox of present invention is capable of overcoming these and other deficiencies of the current state of the art.

SUMMARY OF THE INVENTION

The above discussed disadvantages of the prior art are overcome by the gearbox and manufacturing methods of the present invention.

The miniature gear transmission presented below is comprised of several sections, referred to as lamina, which allow for a highly compact mechanism with high torque density. In certain embodiments, the lamina either contains integrated 3D printed planetary gear stages, a series of spur gear stages, or a combination of both spur and planetary gear stages. In certain embodiments, the design presented below provides a revolute joint between the motor and gear transmission output and is capable of providing several different torque reductions dependent on the gear stages used as the output. The laminar design and placement of gears within the transmission can allow for its seamless integration into its final location, eliminating the need for separate housings.

Thus, it is one aspect of the present invention to provide a gear transmission with a compact design. Such a compact transmission is ideal for applications requiring high torque outputs in a confided space. In certain embodiments, the compactness is achieved through the use of a lamellar design, wherein each section or layer of the gearbox houses multiple components or stages of the gearbox as a whole. In certain embodiments, the gearbox of the present invention is useful as the joints of a prosthetic finger.

It is another aspect of the present invention to provide a compact gearbox with a high torque density. In certain embodiments the high torque density is achieved by making use of a combination of planetary and spur gear stages housed within a lamellar or layered structure.

It is another aspect of the present invention to provide a method of producing such a compact gearbox. In certain embodiments of the present invention the components of the gearbox are produced by additive manufacturing, also referred to as 3D printing. Preferably, direct metal laser sintering (DMSL) is used to manufacture the various components of the gearbox. In various embodiments, the components may be manufactured separately for later assembly, manufactured in a substantially complete state, or some combination of the above.

Thus in one embodiment of the present invention to provide a compact, high torque density gearbox, the gearbox comprising: at least one planetary gear stage; at least one spur gear stage; and wherein said at least one planetary gear stage is housed within a first lamina and said at least one spur gear stage is housed within a second lamina.

It is a second embodiment of the present invention to provide a method of producing such a gearbox, the method comprising: utilizing an additive manufacturing process to produce the components of the gearbox; and assembling said components.

It is another embodiment of the present invention to provide such a method, wherein at least one planetary gear stage is manufactured directly within said first lamina.

It is a third embodiment of the present invention to provide a compact, high torque density gearbox, the gearbox comprising: a first lamina and a second lamina; wherein said first lamina comprises a first planetary gear stage; wherein said first planetary gear stage comprises an output cage; wherein said output cage comprises an output shaft extending perpendicular from said planetary stage and crossing from said first lamina to said second lamina; wherein said second lamina comprises a second planetary gear stage comprising a sun gear and at least two planet gears; wherein said output shaft of said first planetary stage interfaces with said sun gear of said second planetary stage; and wherein said gearbox possesses a torque density of at least 0.15 Nm/m$^3$.

It is another embodiment of the present invention to provide such a compact, high torque density gearbox, further comprising a first pinion gear; wherein said first pinion gear is oriented between said first and second planetary stages, and wherein said output shaft is the rotary shaft of said first pinion gear.

It is yet another embodiment of the present invention to provide such a compact, high torque density gearbox, wherein said at least two planet gears interface with said first pinion gear.

It is still another embodiment of the present invention to provide such a compact, high torque density gearbox, further comprising a third planetary stage housed within said second lamina and a spur gear; wherein said pinion gear interfaces with said spur gear; wherein said spur gear comprises an input shaft; and wherein said input shaft interfaces with a sun gear of said third planetary stage.

These, and other, embodiments of the invention will be better appreciated and understood when considered in conjunction with the following description and the accompanying figures. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

DETAILED DESCRIPTION OF THE INVENTION

Unless otherwise defined, all terms used herein have the same meaning as commonly understood by one of ordinary skill in the art to which this invention belongs. Methods and materials are described herein for use of the present invention; other suitable methods and materials known in the art can also be used. The materials and methods, and examples are illustrative only and not intended to be limiting. All publications, patent applications, patents, and other references mentioned herein are incorporated by reference in their entirety. In case of conflict, the present specification including definitions will control.

"Additive Manufacturing" and "3D printing" are used interchangeably herein, and refer to processes including metal binder jetting, direct energy deposition, and powder bed fusion, including selective laser sintering, selective laser melting, and direct metal laser sintering (DMLS), fused deposit modeling (FDM), fiber reinforced composites, and any other method of 3D printing known in the art or later developed.

The term "interface" refers to the transmission of torque from one component of the gearbox to another. Interfacing may be direct, such as when the teeth of one spur gear mesh with the teeth of another, or indirect, such as through the use of any number of idler gears.

A "lamina" refers to a section or layer of the gearbox, which may house one or more separate planetary or spur gear stages.

The phrase "selecting at least one of a group consisting of X and Y" refers to situations where X is selected alone, Y is selected alone, and where both X and Y are selected together.

Figure 1:
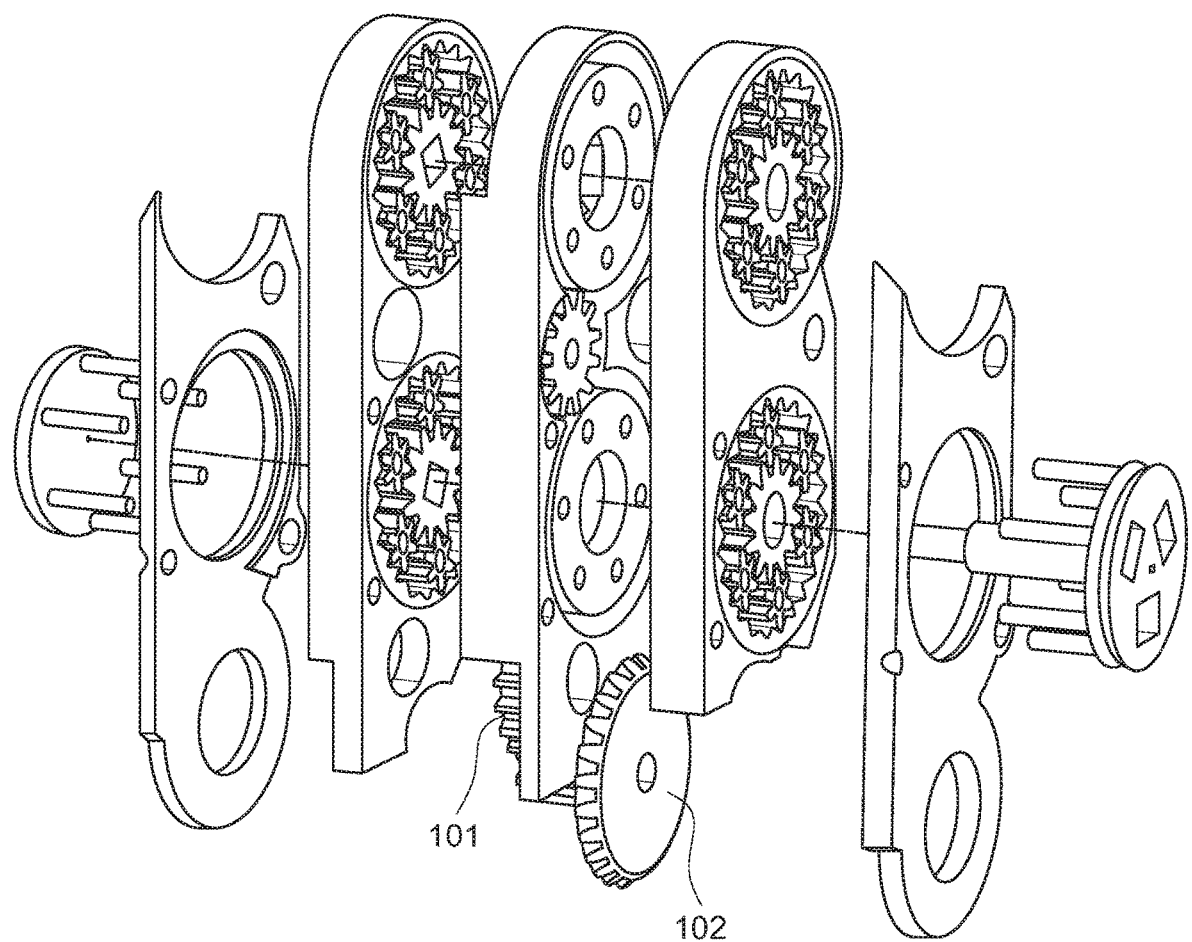
FIG. 1: A partially exploded view of one embodiment of the gearbox of the present invention.

It is one key advantage of the present invention to provide a compact gearbox with high torque density relative to its size. Turning now to FIG. 1, the general layout of one embodiment of the present invention is disclosed in a partially exploded view. The miniaturized gear transmission of this embodiment consists of a combination of spur and planetary gear stages located on different lamina and arranged as shown.

The transmission starts with a bevel gear stage that changes the output shaft direction to be perpendicular to the lamina and also provides a revolute joint between the transmission and motor. This revolute joint can allow for mechanisms that require flexibility between the motor and transmission. A spur gear (101) directly printed onto the larger bevel gear (102) begins the first spur gear stage.

It will be apparent to those having skill in the art such an arrangement has numerous advantages over prior gearboxes. This novel arrangement allows for high speed, low torque transfer to occur within the joint, rather than arranging the gearbox before the transfer point and passing high torque, low speed across the joint. The novel arrangement of the present invention allows the combination of gearbox and motor to be broken into two sections, which straddle the joint. In certain embodiments, this arrangement allows a practitioner to fit a long-combined motor/gearbox within a space anatomically consistent with a small finger joint. Alternately, some combination of the prior technology and the present invention is possible. For example, some gearing may occur prior to passing torque into the joint.

Figure 2:
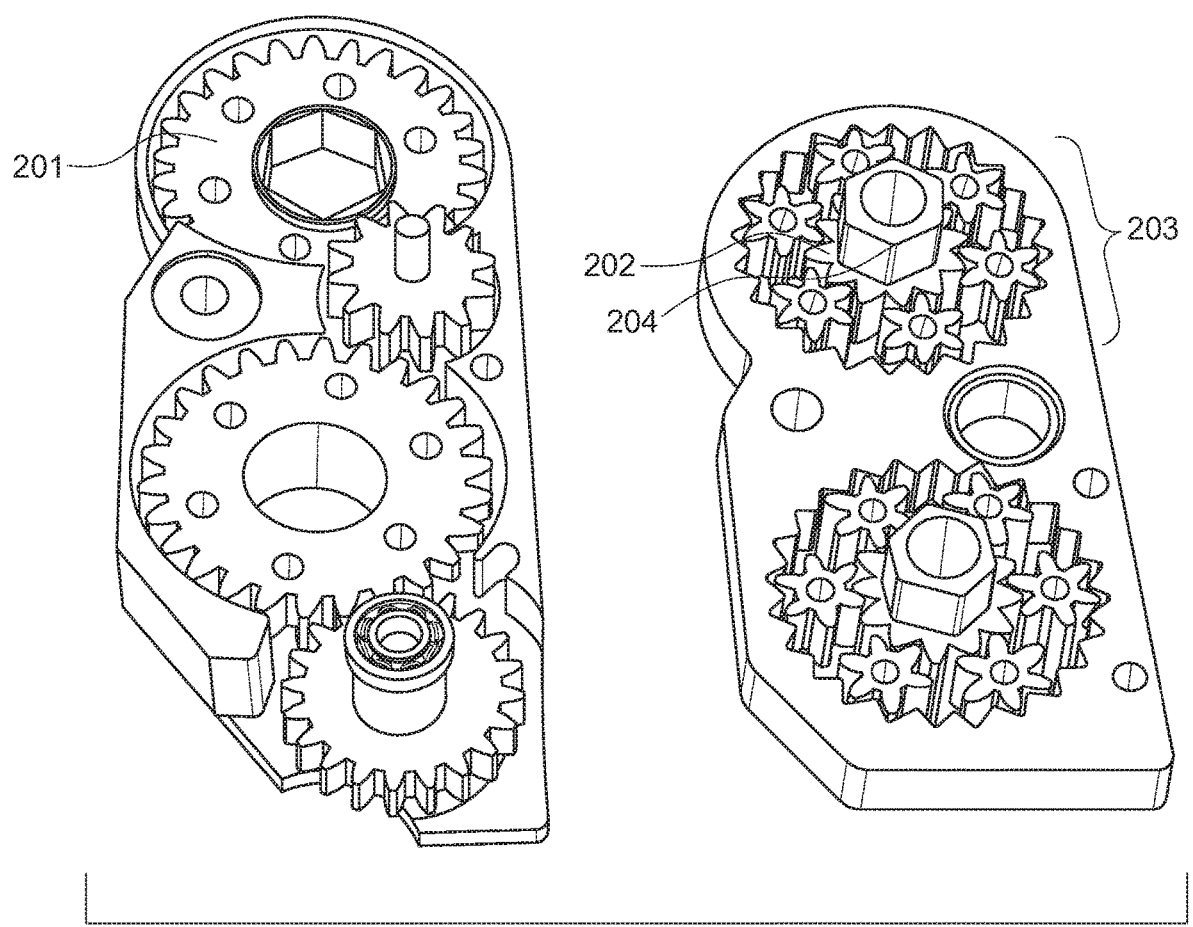
FIG. 2: Two lamina of an embodiment of the gearbox of the present invention.

As illustrated in FIG. 2, which shows the center and an adjacent lamina from a different angle than FIG. 1, the output of each spur stage (201) connects to the sun gear (202) on the adjacent planetary stage (203) through a hexagonal key (204). Also visible in the center of the hexagonal key the opening, through which the output shaft will extend. Idler gears within certain spur stages may be necessary to provide space for bearings.

Figure 3:
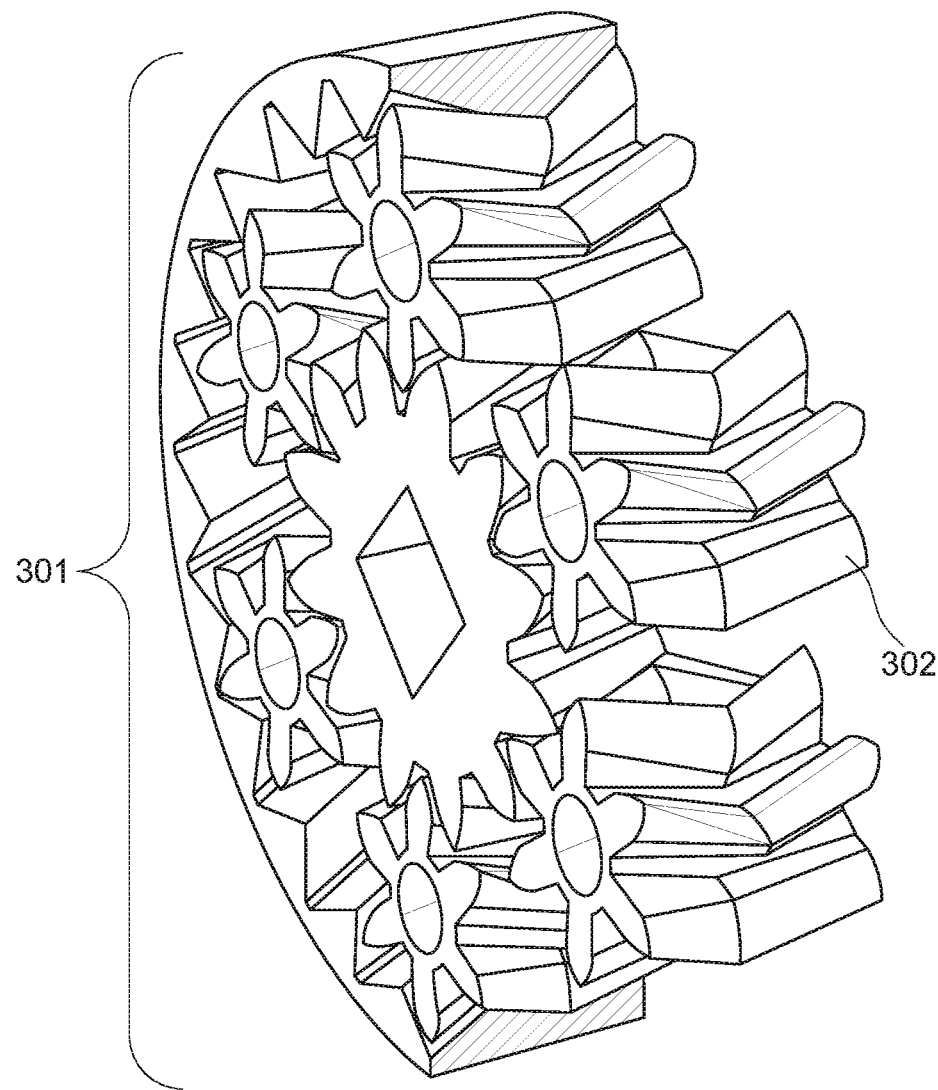
FIG. 3: Partial cutaway of one embodiment of a planetary stage of an embodiment of the present invention.

FIG. 3 illustrates an embodiment of the present invention when a portion of the outer ring of a planetary stage is removed. In this embodiment, the integrated planetary gear stages (301) may consist of spiraled herringbone shaped gears (302). Preferably, such gear stages do not require external assembly, as they may be fabricated as a full gearset via additive manufacturing, which both reduces the number of parts necessary to achieve the torque output of the present invention, while in many cases enabling the use of such small gears. The shape of the gear teeth allows for the printing of a fully functional and self-contained gear stage that also prevents excessive axial displacement between the annulus, sun, and planet gears. In certain embodiments, two or more of these planetary stages print directly onto the exterior lamina of the transmission. The gear transmission presented in this embodiment employs a 3:1 reduction ratio, while it will be apparent to those having skill in the art that different reduction ratios are possible. In alternate embodiments of the present invention, other gear stages may be used in place of, or in addition to, a planetary stage. Such gear stages include, but are not limited to, spur gear stages, worm and wheel gear stages, and cycloidic gear stages.

As will be apparent those having skill in the art, different reduction ratios will impact the number of planet gears which can fit within the planet stages of the miniature gearbox. A 3:1 reduction ratio allows for six planet gears per stage, which in turn means that, at any point, six teeth are bearing the output load. Such an arrangement allows for twice as much output torque to be carried by the system compared to a similar arrangement with only, for example, three planet gears. However, this arrangement also produces twice as much friction as a three-planet-gear system, and is thus less efficient. When determining the reduction ratio, the practitioner must therefore balance the strength and efficiency of the system.

Figure 4:
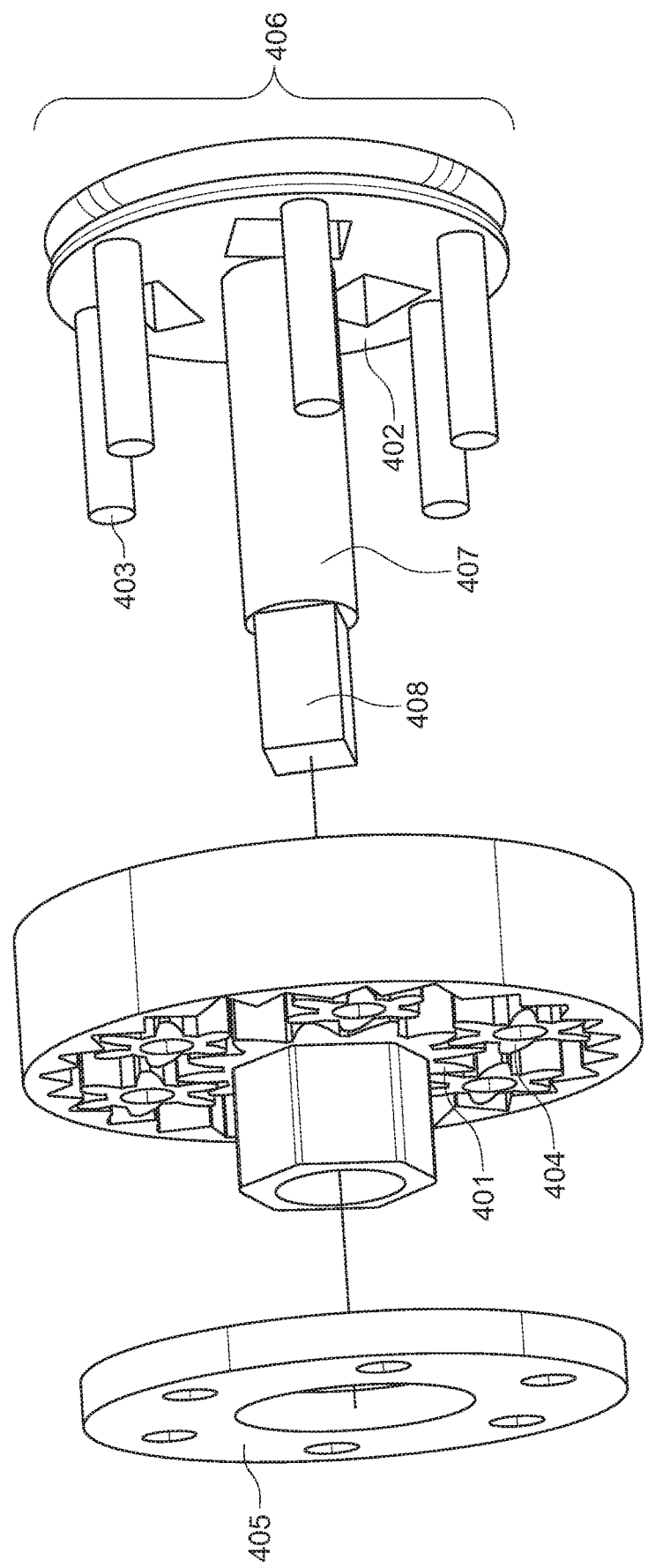
FIG. 4: Partially exploded view of one embodiment of a planetary stage of an embodiment of the present invention.

FIG. 4 illustrates one embodiment of the planetary gear stage. In particular, the figure more clearly shows the output connection for each planetary stage. In this embodiment, the sun gear (401) for each planetary stage serves as the input. The output for each stage consists of a thin circular plate (402) with radially patterned shafts (403) that connect to the planet gears (404). These shafts then connect to a circular plate (405) on the opposite side of the planetary stage from the thin circular plate (402) and forms a cage around the planetary stage. The output cage (406) contains a circular shaft (407) that passes through the interior face of the sun gear. This shaft contains a square key (408) which then attaches to the sun gear of the next planetary stage. These gear cages serve to connect the concentric planetary stages across the left and right laminae, while also providing a rotary shaft for the spur gear stages located within the center lamina.

Figure 5:
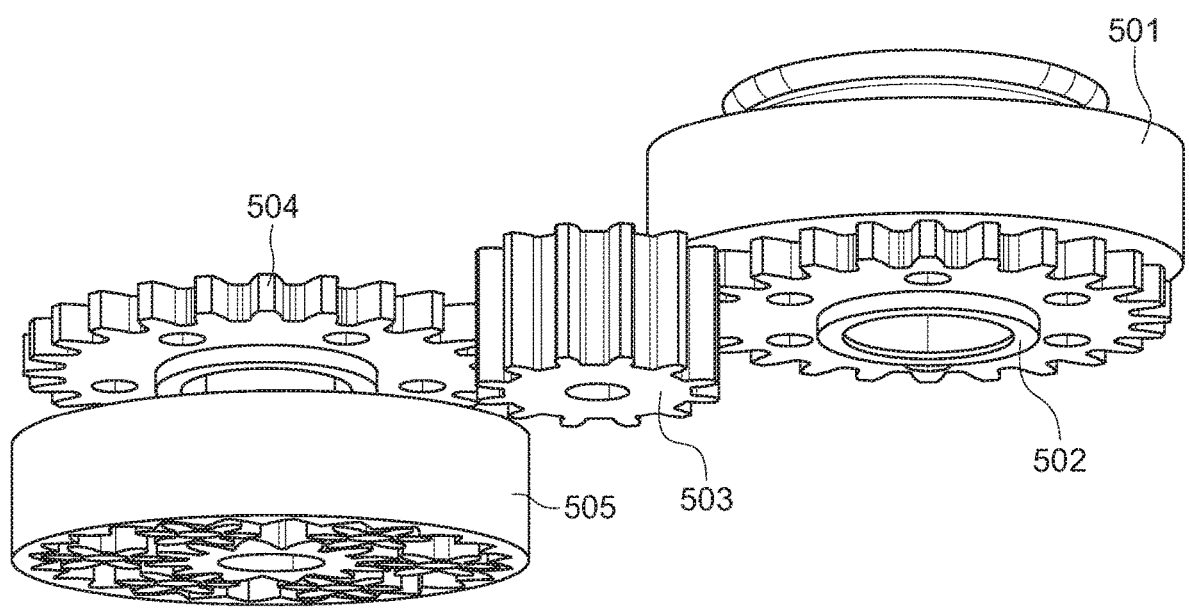
FIG. 5: An illustration of two planetary stages of an embodiment of the present invention linked by a pinion gear.

For the spur stages connecting two diagonal planetary stages across the left and right lamina, the pinion gear for each stage replaces the interior plate on the planet gear cage (405). One possible configuration of such an embodiment is illustrated in FIG. 5, wherein a first planetary gear stage (501) with a pinion gear (502) in lieu of an exterior gear cage connects to an idler gear (503) which in turn interfaces with spur stage (504), similar that of 201, which interfaces with an adjacent planetary stage (505), via the sun gear of such planetary stage. In such an embodiment, idler gears within the spur stages may be necessary to provide spacing for bearings, depending on the application. It is also possible add a gear reduction to these stages. The specific transmission of this embodiment contains a 1:1 reduction.

Figure 6:
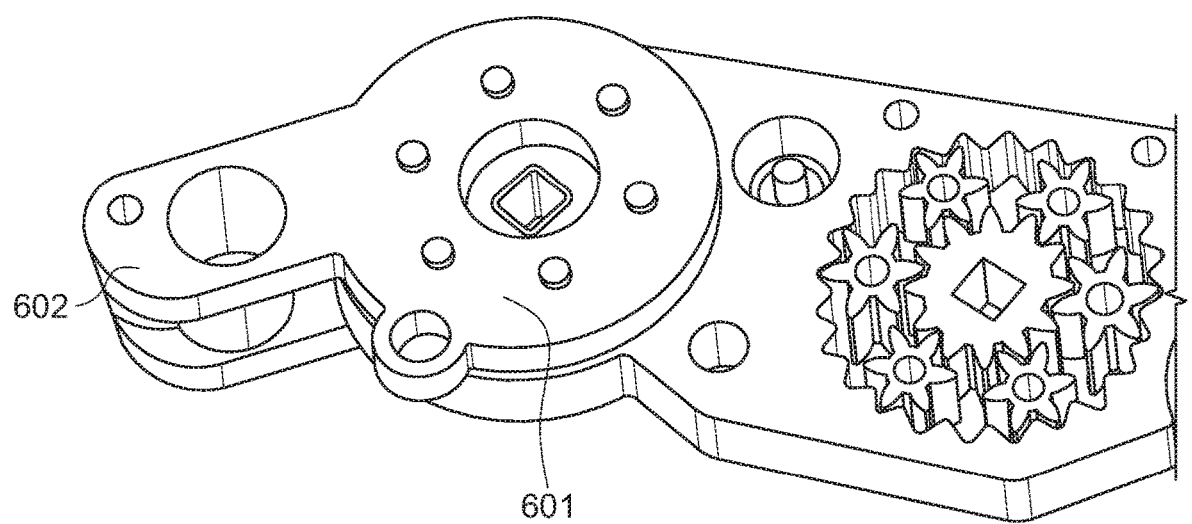
FIG. 6: An illustrative embodiment of the invention in which the final planetary stage provides output through a linkage system.

As illustrated in FIG. 6, the cage (601) on the final planetary stage can act as the transmission output from either exterior or interior side. In various embodiments, this output can then provide torque transmission to a variety of mechanisms, including, but not limited to, a rotary shaft, belt/cable drive, or a linkage system (602). It is also possible to use the exterior face of any of the planetary gear cages as the output due to their location on the side lamina of the transmission in this embodiment.

Figure 9:
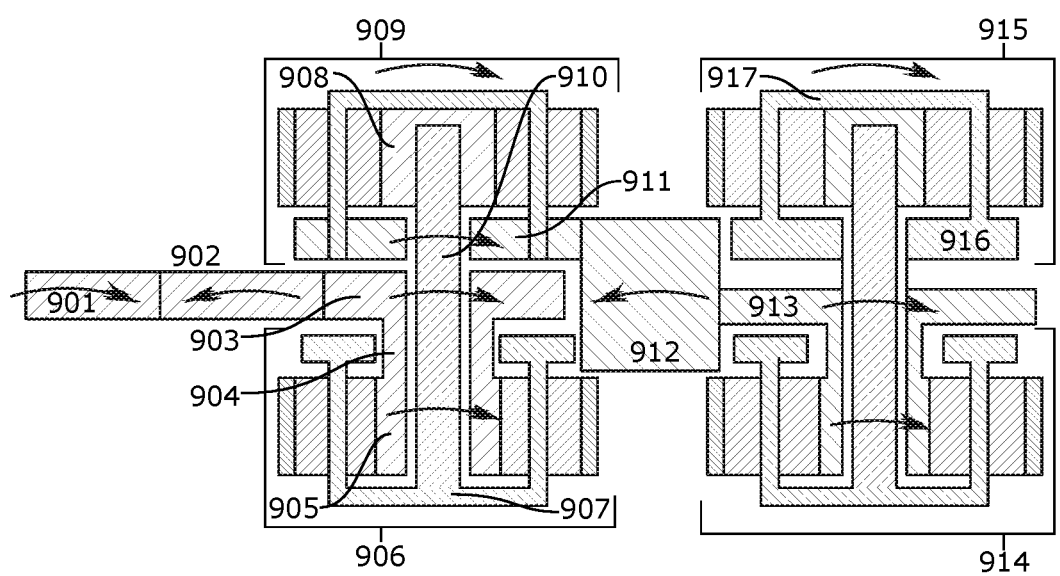
FIG. 9: A cross-section of one embodiment of the gearbox of the present invention.

FIG. 9 illustrates a cross-section of one embodiment of the gearbox of the present invention, wherein arrows indicate the direction or rotation of the various gears. Here, the motor (901) interfaces with an input spur gear (902), which directly interfaces with another spur gear (903) connected via a shaft (904) to the sun gear (905) of the first planetary stage (906). As the first planetary stage turns, the output cage (907) of the first planetary stage interfaces with the sun gear (908) of the second planetary stage (909) via an output shaft (910) running through the center of the first sun gear (905) and across the gearbox. As the second planetary stage turns, it turns the output cage of the second planetary stage, the inner face of which comprises a pinion gear (911) serving as the inner portion of the planetary gear cage for the second planetary stage. The pinion gear (911) directly interfaces with a carrier gear (912), which interfaces with a second input spur gear (913). The system described above is then repeated for the third (914) and fourth (915) planetary stages. It will be apparent to one having skill in the art the final output for this embodiment could be either the inner (916) or outer (917) faces of the planetary cage of the fourth planetary cage.

Figure 7:
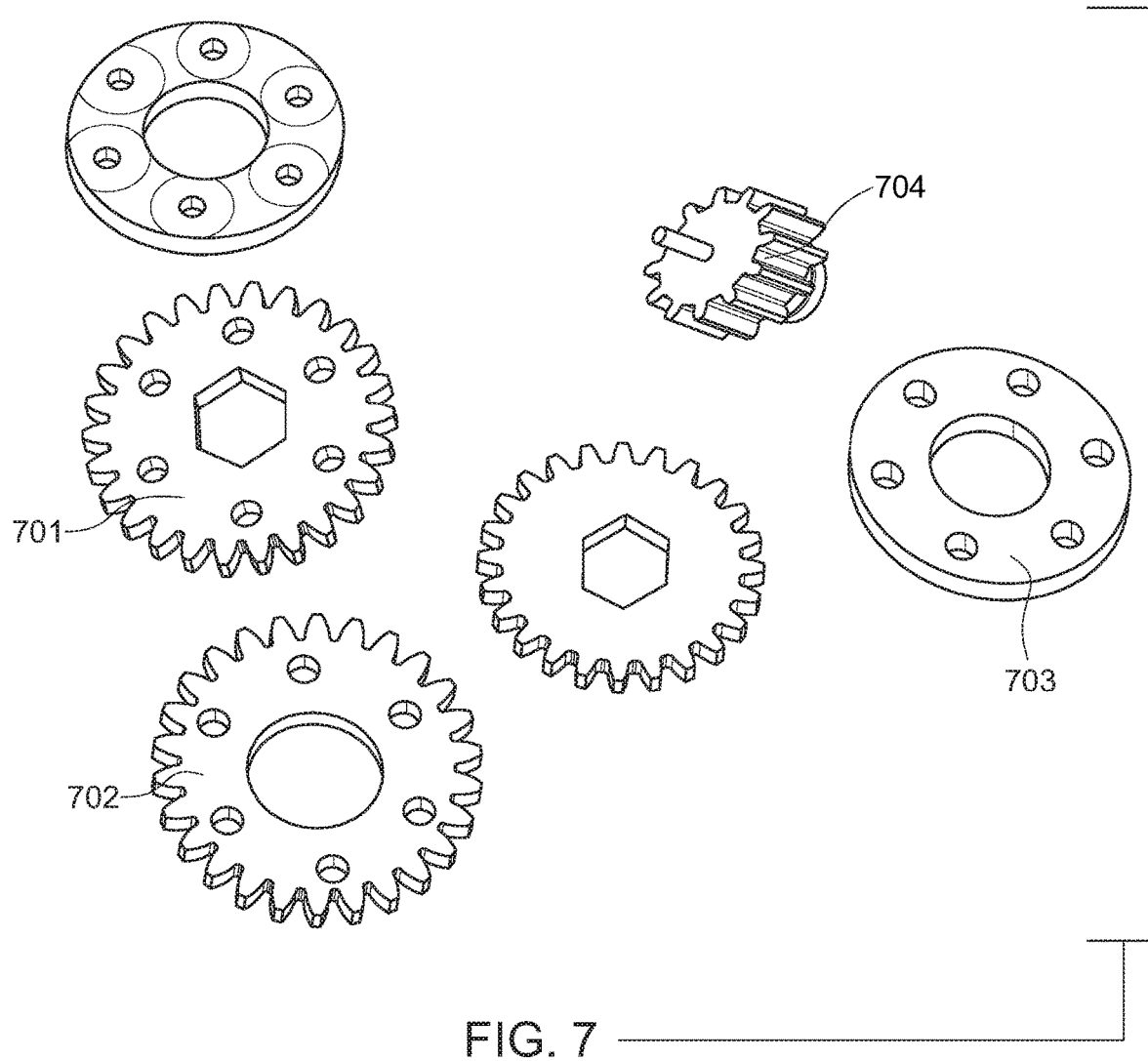
FIG. 7: Various components of one embodiment of the present invention placed on a US Penny for scale.

One of the key aspects of the miniature gearbox of the present invention is the high torque output that is achievable using the components disclosed herein. FIG. 7 illustrates the relative sizes of a spur gear stage (701), pinion cage (702), planetary gear cage (703), and idler gear (704) of one embodiment of the present invention. A more detailed description of the sizes and other characteristics of the various components of one embodiment of the present invention is contained within Table 1.

TABLE 1

Dimensions and Characteristics of Individual Gears.

| Stage | Pitch (teeth/in) | Module (mm/teeth) | Pitch Dimeter (mm) | Teeth | Face Width (mm) | Ratio | Pressure Angle (degrees) |
|---|---|---|---|---|---|---|---|
| Bevel | 84.67 | 0.3 | 3.6 | 12 | 1 | 1.5 | 20 |
|  |  |  | 5.4 | 18 | 1 |  |  |
| Spur | 76.2 | 0.333 | 3 | 9 | 1 | 3 | 20 |
|  |  |  | 6.333 | 19 | 1 |  |  |
|  |  |  | 9 | 27 | 1 |  |  |
| Planetary | 67.73 | 0.375 | 9 | 24 | 2 | 4 | 35 |
|  |  |  | 3 | 8 | 2 |  |  |
|  |  |  | 3 | 8 | 2 |  |  |
| Planetary | 67.73 | 0.375 | 9 | 24 | 2 | 4 | 35 |
|  |  |  | 3 | 8 | 2 |  |  |
|  |  |  | 3 | 8 | 2 |  |  |
| Spur | 67.73 | 0.375 | 8.25 | 22 | 1 | 1.182 | 20 |
|  |  |  | 5.25 | 14 | 1 |  |  |
|  |  |  | 9.75 | 26 | 1.3 |  |  |
| Planetary | 67.73 | 0.375 | 9 | 24 | 2.9 | 4 | 35 |
|  |  |  | 3 | 8 | 2.9 |  |  |
|  |  |  | 3 | 8 | 2.9 |  |  |

As will be apparent to those having skill in the art, the torque density of a power transmission is defined as the amount of torque capacity per unit volume. One of the key limits for determining the intermittent torque limit of a system is the load rating of the bearings used within it. In certain embodiments of the present invention, the miniaturized gearbox possesses a torque density of at least 0.150 Nm/m$^3$, 0.17305 Nm/m$^3$, 0.7794 Nm/m$^3$, 0.8105 Nm/m$^3$, or 6.93140 Nm/m$^3$.

Furthermore, those having skill in the art will appreciate that, by using a laminar design to connect subsequent gear stages, high torque density is possible by directing the output shaft of the planetary stages through the sun gear and behind the input shaft. This allows the input shafts of the planetary stages to face towards the interior of the gearbox and provides a rotary shaft for the spur stages housed in between the planetary stages. This also allows for a robust configuration of spur gears, as it provides bearing mounts at both ends of the spur gears. By housing spur stages in between planetary stages, the laminar configuration allows for the addition of several gear stages with very small increases in overall volume.

Figure 8:
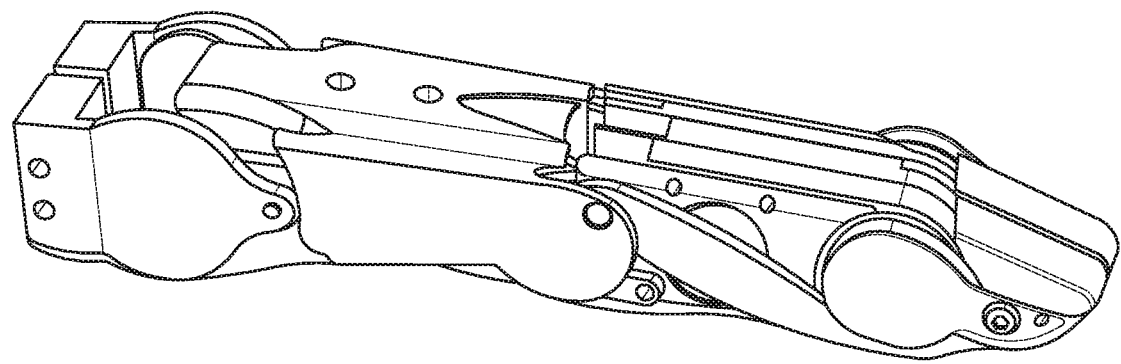
FIG. 8: A prosthetic figure comprising the compact gearbox of the present invention.

As illustrated in FIG. 8, one application of the laminar gearbox presented in the invention, which has been successfully reduced to practice, is in powered finger prostheses with full articulation. Use of prior-art gearboxes are not able to produce such a prosthesis with anatomically correct articulations and proportions for each of the MCP, PIP, and DIP joints while delivering both high torque and speed. The high torque density and novel configuration of alternating spur and planetary gear stages of the preferred embodiment allow for sizes roughly corresponding to the 25-50th percentile female index finger lengths and full integration into the medial phalanx.

In certain embodiments of the present invention, the miniature gearbox is produced primarily through the use of additive manufacturing. Preferably, the laminar transmission is manufactured using DMLS, which opens the possibility of fully functional, miniature power transmissions for applications with high torque densities. DMLS involves the addition of a thin layer of powdered material onto which a high-power laser applies a two-dimensional pattern. Successive layers fuse together to form the final part. DMLS printing can employ various plastics and metals. Part accuracies using DMLS can approach 20 μm. This can allow for gears with unconventional pitches and pressure angles, as well as accompanying shafts and keyways that would be difficult or impractical to manufacture on a miniature scale with traditional processes, such as die casting or gear hobbing. As noted in the table above, certain stages in the preferred embodiment employ pressure angles as high as 35 degrees, which is both important for maintaining the compact form-factor of the present gearbox, and also difficult, if not impossible, to achieve using standard manufacturing processes.

Preferably, the material for the miniature gear transmission presented herein is Maraging Steel. The high tensile and yield strengths can give equivalent or higher torque capabilities for gears with much higher diametral pitches such as those in FIG. 7. However, any material which possesses the requisite characteristics could be used.

In certain embodiments, the miniature gear transmission employs a laminar, stackable design that allows for quick assembly and replacement of worn/damaged pieces. Preferably, the planetary stages print directly onto their respective laminae of the gear transmission. This also ensures a minimal amount of support structure removal during the post-processing phase. In certain cases, a series of dowel pins may be used provide alignment between the pieces. Alternately, it is possible to have these alignment pins directly printed onto the exterior pieces. A variety of fasteners can contain the gear transmission, including commercially available miniature screws, spring pins, or retaining rings. In order to have better access to the internal gears, the transmission of one embodiment uses a set of #0 screws and accompanying standoff.

Methods and components are described herein. However, methods and components similar or equivalent to those described herein can be also used to obtain variations of the present invention. The materials, articles, components, methods, and examples are illustrative only and not intended to be limiting.

Although only a few embodiments have been disclosed in detail above, other embodiments are possible, and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art.

Having illustrated and described the principles of the invention in exemplary embodiments, it should be apparent to those skilled in the art that the described examples are illustrative embodiments and can be modified in arrangement and detail without departing from such principles. Techniques from any of the examples can be incorporated into one or more of any of the other examples. It is intended that the specification and examples be considered as exemplary only, with a true scope and spirit of the invention being indicated by the following claims.

We claim:

1. A compact, high torque density gearbox, the gearbox comprising:
   a. a first lamina and a second lamina;
   b. wherein said first lamina comprises a first planetary gear stage;
      i. wherein said first planetary gear stage comprises an output cage;
      ii. wherein said output cage comprises an output shaft extending perpendicular from said planetary stage and crossing from said first lamina to said second lamina;
   c. wherein said second lamina comprises a second planetary gear stage comprising a sun gear and at least two planet gears;
   d. wherein said output shaft of said first planetary stage interfaces with said sun gear of said second planetary stage; and
   e. wherein said gearbox possesses a torque density of at least 0.15 Nm/m$^3$.

2. The compact, high torque density gearbox of claim 1, further comprising a first pinion gear; wherein said first pinion gear is oriented between said first and second planetary stages, and wherein said output shaft is the rotary shaft of said first pinion gear.

3. The compact high torque density gearbox of claim 2, wherein said at least two planet gears interface with said first pinion gear.

4. The compact, high density gearbox of claim 3, further comprising a third planetary stage housed within said second lamina and a spur gear; wherein said pinion gear interfaces with said spur gear; wherein said spur gear comprises an input shaft; and wherein said input shaft interfaces with a sun gear of said third planetary stage.

* * * * *